(12) United States Patent
Ferguson et al.

(10) Patent No.: US 7,144,389 B2
(45) Date of Patent: Dec. 5, 2006

(54) SAFETY SHIELD FOR MEDICAL NEEDLES

(75) Inventors: F. Mark Ferguson, Salt Lake City, UT (US); Daniel K. Smith, Woods Cross, UT (US)

(73) Assignee: Tyco Healthcare Group, LP, Mansfield, MA (US)

( * ) Notice: Subject to any disclaimer, the term of this patent is extended or adjusted under 35 U.S.C. 154(b) by 244 days.

(21) Appl. No.: 10/307,812

(22) Filed: Dec. 2, 2002

(65) Prior Publication Data

US 2003/0088215 A1 May 8, 2003

Related U.S. Application Data

(63) Continuation-in-part of application No. 10/164,944, filed on Jun. 6, 2002, now Pat. No. 7,029,461, which is a continuation-in-part of application No. 09/892,593, filed on Jun. 27, 2001.

(60) Provisional application No. 60/275,886, filed on Mar. 14, 2001.

(51) Int. Cl.
*A61M 5/32* (2006.01)
(52) U.S. Cl. ........................................ 604/198
(58) Field of Classification Search ................ 604/110, 604/164.08, 192, 198, 263, 197; 128/919
See application file for complete search history.

(56) References Cited

U.S. PATENT DOCUMENTS

| | | |
|---|---|---|
| 1,779,451 A | 10/1930 | Sponsel |
| 2,559,474 A | 7/1951 | Son ............................. 128/215 |
| 2,700,385 A | 1/1955 | Ortiz .......................... 128/215 |
| 2,836,942 A | 6/1958 | Miskel .......................... 53/25 |
| 2,854,976 A | 10/1958 | Heydrich .................... 128/221 |
| 2,953,243 A | 9/1960 | Roehr ......................... 206/43 |
| 3,021,942 A | 2/1962 | Hamilton ..................... 206/43 |
| 3,073,307 A | 1/1963 | Stevens ....................... 128/221 |
| 3,074,542 A | 1/1963 | Myerson et al. .............. 206/43 |
| 3,255,873 A | 6/1966 | Speelman ..................... 206/56 |
| 3,294,231 A | 12/1966 | Vanderbeck .................. 206/63 |
| 3,323,523 A | 6/1967 | Scislowicz et al. ......... 128/214 |
| 3,329,146 A | 7/1967 | Waldman, Jr. .............. 128/221 |
| 3,333,682 A | 8/1967 | Burke .......................... 206/43 |
| 3,367,488 A | 2/1968 | Hamilton ..................... 206/63 |
| 3,485,239 A | 12/1969 | Vanderbeck ................. 128/218 |
| 3,537,452 A | 11/1970 | Wilks .......................... 128/214 |
| 3,587,575 A | 6/1971 | Lichtenstein ................ 128/215 |
| 3,610,240 A | 10/1971 | Haräutuneian .............. 128/214 |
| 3,658,061 A | 4/1972 | Hall ........................... 128/214 |

(Continued)

FOREIGN PATENT DOCUMENTS

EP 0 144 483 6/1985

(Continued)

*Primary Examiner*—Catherine S. Williams

(57) ABSTRACT

A medical needle shield apparatus is provided that includes a first cylinder, such as, for example, a shield that is extensible from a retracted position to an extended position for enclosing a distal end of a needle of a medical needle device. The shield includes a collar that is mounted to the medical needle device. The shield further includes a proximal portion extending from the collar and a distal portion extending from the proximal portion. The distal portion is configured to enclose the distal end of the needle in the extended position. The proximal portion includes an engagement surface that is engageable to urge the shield from the retracted position to the extended position. The collar includes a guard extending therefrom and is disposed adjacent to the distal portion of the shield in the retracted position such that inadvertent extension of the shield, via engagement of the distal portion, is prevented.

30 Claims, 14 Drawing Sheets

U.S. PATENT DOCUMENTS

| | | | |
|---|---|---|---|
| 3,828,775 A | 8/1974 | Armel | 128/218 |
| 3,840,008 A | 10/1974 | Noiles | 128/221 |
| 3,890,971 A | 6/1975 | Leeson et al. | 128/218 |
| 3,904,033 A | 9/1975 | Haerr | 206/349 |
| 3,934,722 A | 1/1976 | Goldberg | 206/365 |
| 3,968,876 A | 7/1976 | Brookfield | 206/365 |
| 4,040,419 A | 8/1977 | Goldman | 128/215 |
| 4,106,621 A | 8/1978 | Sorenson | 206/365 |
| 4,113,090 A | 9/1978 | Carstens | 206/365 |
| 4,139,009 A | 2/1979 | Alvarez | 128/218 |
| 4,175,008 A | 11/1979 | White | 435/295 |
| 4,270,536 A | 6/1981 | Lemelson | 128/218 |
| 4,300,678 A | 11/1981 | Gyure et al. | 206/364 |
| 4,375,849 A | 3/1983 | Hanifl | 206/366 |
| 4,430,082 A | 2/1984 | Schwabacher | 604/263 |
| 4,592,744 A | 6/1986 | Jagger et al. | 604/192 |
| 4,634,428 A | 1/1987 | Cuu | 604/110 |
| 4,643,722 A | 2/1987 | Smith, Jr. | 604/192 |
| 4,659,330 A | 4/1987 | Nelson et al. | 604/192 |
| 4,664,259 A | 5/1987 | Landis | 206/365 |
| 4,664,654 A | 5/1987 | Strauss | 604/198 |
| 4,681,567 A | 7/1987 | Masters et al. | 604/198 |
| 4,695,274 A | 9/1987 | Fox | 604/198 |
| 4,702,738 A | 10/1987 | Spencer | 604/198 |
| 4,723,943 A | 2/1988 | Spencer | 604/198 |
| 4,728,320 A | 3/1988 | Chen | 604/110 |
| 4,728,321 A | 3/1988 | Chen | 604/110 |
| 4,731,059 A | 3/1988 | Wanderer et al. | 604/192 |
| 4,735,311 A | 4/1988 | Lowe et al. | 206/365 |
| 4,735,618 A | 4/1988 | Hagen | 604/192 |
| 4,737,144 A | 4/1988 | Choksi | 604/198 |
| 4,738,663 A | 4/1988 | Bogan | 604/198 |
| 4,743,233 A | 5/1988 | Schneider | 604/192 |
| 4,747,836 A | 5/1988 | Luther | 604/198 |
| 4,747,837 A | 5/1988 | Hauck | 604/198 |
| 4,772,272 A | 9/1988 | McFarland | 604/198 |
| 4,778,453 A | 10/1988 | Lopez | 604/110 |
| 4,781,697 A | 11/1988 | Slaughter | 604/192 |
| 4,782,841 A | 11/1988 | Lopez | 128/164 |
| 4,790,828 A | 12/1988 | Dombrowski et al. | 604/198 |
| 4,795,432 A | 1/1989 | Karczmer | 604/110 |
| 4,795,443 A | 1/1989 | Permenter et al. | 604/198 |
| 4,801,295 A | 1/1989 | Spencer | 604/198 |
| 4,804,372 A | 2/1989 | Laico et al. | 604/198 |
| 4,813,426 A | 3/1989 | Haber et al. | 128/763 |
| 4,816,022 A | 3/1989 | Poncy | 604/198 |
| 4,816,024 A | 3/1989 | Sitar et al. | 604/192 |
| 4,819,659 A | 4/1989 | Sitar | 128/764 |
| 4,820,277 A | 4/1989 | Norelli | 604/192 |
| 4,826,490 A | 5/1989 | Byrne et al. | 604/198 |
| 4,826,491 A | 5/1989 | Schramm | 604/198 |
| 4,838,871 A | 6/1989 | Luther | 604/192 |
| 4,840,619 A | 6/1989 | Hughes | 604/187 |
| 4,842,587 A | 6/1989 | Poncy | 604/198 |
| 4,846,796 A | 7/1989 | Carrell et al. | 604/110 |
| 4,846,811 A | 7/1989 | Vanderhoof | 604/263 |
| 4,850,968 A | 7/1989 | Romano | 604/110 |
| 4,850,976 A | 7/1989 | Heinrich et al. | 604/192 |
| 4,850,977 A | 7/1989 | Bayless | 604/198 |
| 4,850,978 A | 7/1989 | Dudar et al. | 604/201 |
| 4,850,994 A | 7/1989 | Zerbst et al. | 604/198 |
| 4,850,996 A | 7/1989 | Cree | 604/198 |
| 4,858,607 A | 8/1989 | Jordan et al. | 128/314 |
| 4,863,434 A | 9/1989 | Bayless | 604/198 |
| 4,863,435 A * | 9/1989 | Sturman et al. | 604/198 |
| 4,863,436 A | 9/1989 | Glick | 604/198 |
| 4,867,172 A | 9/1989 | Haber et al. | 128/763 |
| 4,867,746 A | 9/1989 | Dufresne | 604/192 |
| 4,872,552 A | 10/1989 | Unger | 206/365 |
| 4,874,382 A | 10/1989 | Lindemann et al. | 604/195 |
| 4,874,383 A | 10/1989 | McNaughton | 604/198 |
| 4,874,384 A | 10/1989 | Nunez | 604/198 |
| 4,883,469 A | 11/1989 | Glazier | 604/192 |
| 4,886,503 A | 12/1989 | Miller | 604/192 |
| 4,887,998 A | 12/1989 | Martin et al. | 604/110 |
| 4,888,001 A | 12/1989 | Schoenberg | 604/162 |
| 4,892,107 A | 1/1990 | Haber | 128/763 |
| 4,892,521 A | 1/1990 | Laico et al. | 604/192 |
| 4,898,589 A | 2/1990 | Dolgin et al. | 604/198 |
| 4,900,309 A | 2/1990 | Netherton et al. | 604/192 |
| 4,904,244 A | 2/1990 | Harsh et al. | 604/187 |
| 4,911,694 A | 3/1990 | Dolan | 604/198 |
| 4,911,706 A | 3/1990 | Levitt | 604/198 |
| 4,915,697 A * | 4/1990 | DuPont | 604/192 |
| 4,927,018 A | 5/1990 | Yang et al. | 206/365 |
| 4,929,241 A | 5/1990 | Kulli | 604/263 |
| 4,935,012 A | 6/1990 | Magre et al. | 604/192 |
| 4,935,013 A | 6/1990 | Haber et al. | 604/192 |
| 4,936,830 A | 6/1990 | Verlier | 604/110 |
| 4,944,397 A | 7/1990 | Miller | 206/365 |
| 4,944,731 A | 7/1990 | Cole | 604/192 |
| 4,950,249 A | 8/1990 | Jagger et al. | 604/192 |
| 4,950,250 A | 8/1990 | Haber et al. | 604/192 |
| 4,978,344 A | 12/1990 | Dombrowski et al. | 604/198 |
| 4,982,842 A | 1/1991 | Hollister | 206/365 |
| 4,985,021 A | 1/1991 | Straw et al. | 604/198 |
| 4,994,041 A | 2/1991 | Dombrowski et al. | 604/164 |
| 5,000,744 A | 3/1991 | Hoffman et al. | 604/232 |
| 5,015,240 A | 5/1991 | Soproni et al. | 604/192 |
| 5,057,089 A | 10/1991 | Greco | 604/198 |
| 5,059,180 A | 10/1991 | McLees | 604/110 |
| 5,092,851 A | 3/1992 | Ragner | 604/192 |
| 5,108,379 A | 4/1992 | Dolgin et al. | 604/198 |
| RE34,045 E | 8/1992 | McFarland | 604/198 |
| 5,135,509 A | 8/1992 | Olliffe | 604/192 |
| 5,139,489 A | 8/1992 | Hollister | 604/192 |
| 5,147,303 A | 9/1992 | Martin | 604/110 |
| 5,154,285 A | 10/1992 | Hollister | 206/365 |
| 5,176,655 A | 1/1993 | McCormick et al. | 604/198 |
| 5,176,656 A | 1/1993 | Bayless | 604/198 |
| 5,193,552 A | 3/1993 | Columbus et al. | 128/760 |
| 5,195,983 A | 3/1993 | Boese | 604/192 |
| 5,209,739 A | 5/1993 | Talalay | 604/195 |
| 5,232,454 A | 8/1993 | Hollister | 604/192 |
| 5,232,455 A | 8/1993 | Hollister | 604/192 |
| 5,242,417 A | 9/1993 | Paudler | 604/192 |
| 5,242,418 A | 9/1993 | Weinstein | 604/192 |
| 5,246,427 A | 9/1993 | Sturman et al. | 604/192 |
| 5,246,428 A | 9/1993 | Falknor | 604/198 |
| 5,250,031 A | 10/1993 | Kaplan et al. | 604/110 |
| 5,254,099 A | 10/1993 | Kuracina et al. | 604/198 |
| 5,256,152 A | 10/1993 | Marks | 604/198 |
| 5,256,153 A | 10/1993 | Hake | 604/198 |
| 5,277,311 A | 1/1994 | Hollister | 206/365 |
| 5,290,255 A | 3/1994 | Vallelunga et al. | 604/197 |
| 5,304,137 A | 4/1994 | Fluke | 604/110 |
| 5,312,369 A | 5/1994 | Arcusin et al. | 604/192 |
| 5,334,158 A | 8/1994 | McLees | 604/110 |
| 5,348,544 A | 9/1994 | Sweeney et al. | 604/192 |
| 5,356,392 A | 10/1994 | Firth et al. | 604/198 |
| 5,403,283 A | 4/1995 | Luther | 604/164 |
| 5,403,286 A | 4/1995 | Lockwood, Jr. | 604/110 |
| 5,407,436 A | 4/1995 | Toft et al. | 604/195 |
| 5,411,492 A | 5/1995 | Sturman et al. | 604/263 |
| 5,423,765 A | 6/1995 | Hollister | 604/192 |
| 5,423,766 A | 6/1995 | Di Cesare | 604/192 |
| 5,425,720 A | 6/1995 | Rogalsky et al. | 604/198 |
| 5,447,501 A | 9/1995 | Karlsson et al. | 604/198 |
| 5,466,223 A | 11/1995 | Bressler et al. | 604/110 |
| 5,480,385 A | 1/1996 | Thorne et al. | 604/110 |
| 5,487,733 A | 1/1996 | Caizza et al. | 604/110 |
| 5,487,734 A | 1/1996 | Thorne et al. | 604/195 |
| 5,490,841 A | 2/1996 | Landis | 604/110 |
| 5,498,243 A | 3/1996 | Vallelunga et al. | 604/197 |

| | | | |
|---|---|---|---|
| 5,531,694 A | 7/1996 | Clemens et al. | 604/110 |
| 5,533,980 A | 7/1996 | Sweeney et al. | 604/192 |
| 5,538,508 A | 7/1996 | Steyn | 604/192 |
| 5,542,927 A | 8/1996 | Thorne et al. | 604/110 |
| 5,549,568 A | 8/1996 | Shields | 604/192 |
| 5,549,570 A | 8/1996 | Rogalsky | 604/198 |
| 5,549,708 A | 8/1996 | Thorne et al. | 604/110 |
| 5,562,629 A | 10/1996 | Haughton et al. | 604/158 |
| 5,562,631 A | 10/1996 | Bogert | 604/164 |
| 5,573,510 A | 11/1996 | Isaacson | 604/158 |
| 5,584,816 A | 12/1996 | Gyure et al. | 604/192 |
| 5,584,818 A | 12/1996 | Morrison | 604/197 |
| 5,599,318 A | 2/1997 | Sweeney et al. | 604/263 |
| 5,611,782 A * | 3/1997 | Haedt | 604/198 |
| 5,643,220 A | 7/1997 | Cosme | 604/192 |
| 5,665,075 A * | 9/1997 | Gyure et al. | 604/263 |
| 5,672,161 A | 9/1997 | Allen et al. | 604/263 |
| 5,695,474 A | 12/1997 | Daugherty | 604/162 |
| 5,695,477 A | 12/1997 | Sfikas | 604/241 |
| 5,700,249 A | 12/1997 | Jenkins | 604/263 |
| 5,735,827 A | 4/1998 | Adwers et al. | 604/263 |
| 5,738,665 A | 4/1998 | Caizza et al. | 604/263 |
| 5,746,718 A | 5/1998 | Steyn | 604/192 |
| 5,746,726 A | 5/1998 | Sweeney et al. | 604/263 |
| 5,755,699 A | 5/1998 | Blecher et al. | 604/198 |
| 5,814,018 A | 9/1998 | Elson et al. | 604/110 |
| 5,817,064 A * | 10/1998 | DeMarco et al. | 604/198 |
| 5,823,997 A | 10/1998 | Thorne | 604/110 |
| 5,843,041 A | 12/1998 | Hake et al. | 604/198 |
| 5,910,130 A * | 6/1999 | Caizza et al. | 604/110 |
| 5,919,168 A | 7/1999 | Wheeler | 604/198 |
| 5,925,020 A | 7/1999 | Nestell | 604/198 |
| 5,951,522 A | 9/1999 | Rosato et al. | 604/177 |
| 5,957,892 A | 9/1999 | Thorne | 604/162 |
| 5,980,488 A | 11/1999 | Thorne | 604/110 |
| 6,015,397 A | 1/2000 | Elson et al. | 604/192 |
| 6,036,675 A | 3/2000 | Thorne et al. | 604/232 |
| 6,149,629 A | 11/2000 | Wilson et al. | 604/198 |
| 6,171,284 B1 | 1/2001 | Kao et al. | 604/192 |
| RE37,110 E | 3/2001 | Hollister | 206/365 |
| 6,224,576 B1 | 5/2001 | Thorne et al. | 604/198 |
| RE37,252 E | 7/2001 | Hollister | 206/364 |
| 6,254,575 B1 | 7/2001 | Thorne, Jr. et al. | 604/198 |
| 6,280,420 B1 | 8/2001 | Ferguson et al. | 604/198 |
| 6,334,857 B1 | 1/2002 | Hollister et al. | 604/263 |
| 6,582,397 B1 * | 6/2003 | Alesi et al. | 604/110 |
| 2001/0039401 A1 | 11/2001 | Ferguson et al. | 604/198 |
| 2002/0072716 A1 | 6/2002 | Barrus et al. | 604/192 |
| 2003/0004465 A1 | 1/2003 | Ferguson et al. | 604/198 |

FOREIGN PATENT DOCUMENTS

| | | |
|---|---|---|
| EP | 0 344 606 A2 | 12/1989 |
| EP | 0 457 477 B1 | 11/1991 |
| EP | 0 485 345 B1 | 5/1992 |
| EP | 0 533 308 A1 | 3/1993 |
| EP | 0 585 391 B1 | 3/1994 |
| EP | 0 597 857 B1 | 5/1994 |
| EP | 0 603 365 B1 | 6/1994 |
| EP | 0 626 924 B1 | 12/1994 |
| EP | 0 654 281 B1 | 5/1995 |
| EP | 0 705 613 B1 | 4/1996 |
| EP | 0 713 710 A1 | 5/1996 |
| EP | 0 807 443 A2 | 11/1997 |
| EP | 0 815 888 A2 | 1/1998 |
| EP | 0 815 890 A2 | 1/1998 |
| EP | 0 819 441 A1 | 1/1998 |
| EP | 0 832 659 A2 | 4/1998 |
| EP | 0 832 660 A2 | 4/1998 |
| EP | 1 092 443 A2 | 4/2001 |
| EP | 1 116 493 A1 | 7/2001 |
| GB | 1233302 | 5/1971 |
| GB | 2 283 429 A | 5/1995 |
| GB | 2 369 779 | 12/2002 |
| JP | 10-76007 | 3/1998 |
| JP | 10-127765 | 5/1998 |
| WO | WO 87/07162 | 12/1987 |
| WO | WO 89/07955 | 9/1989 |
| WO | WO 93/17732 | 9/1993 |
| WO | WO 94/19036 | 9/1994 |
| WO | WO 97/31666 | 4/1997 |
| WO | WO 98/07463 | 2/1998 |
| WO | WO 98/10816 | 3/1998 |
| WO | WO 98/11928 | 3/1998 |
| WO | WO 98/13081 | 4/1998 |
| WO | WO 00/16832 | 3/2000 |
| WO | WO 00/38765 | 6/2000 |
| WO | WO 01/32241 A1 | 5/2001 |
| WO | WO 01/32244 A1 | 5/2001 |

* cited by examiner

SAFETY SHIELD FOR MEDICAL NEEDLES

CROSS-REFERENCE TO RELATED APPLICATIONS

This patent application is a continuation-in-part of U.S. Utility patent application Ser. No. 10/164,944, filed in the U.S. Patent and Trademark Office on Jun. 6, 2002 now U.S. Pat. No. 7,029,461 by Ferguson et al., which is a continuation-in-part of U.S. Utility patent application Ser. No. 09/892,593 filed in the U.S. Patent and Trademark Office on Jun. 27, 2001 by Ferguson et al., which claims priority from U.S. Provisional Patent Application Ser. No. 60/275,886 filed in the U.S. Patent and Trademark Office on Mar. 14, 2001 by Thome et al., the entire contents of each of these disclosures being hereby incorporated by reference herein.

BACKGROUND

1. Technical Field

The present disclosure generally relates to safety shields for medical needles, and more particularly, to extensible safety shields that employ a manual actuator to configure the safety shield from a retracted position into an extended position.

2. Description of the Related Art

Problems associated with inadvertent needle sticks are well known in the art of blood sampling, percutaneous medication injection and other medical procedures involving use of medical needles. Significant attention has been focused on needle stick problems due to the contemporary sensitivity of exposure to AIDS, Hepatitis and other serious blood-borne pathogens.

Procedures for removing a needle from a patient commonly require a clinician to use one hand to place pressure at the wound site where a needle is being withdrawn, while removing the needle device with the other hand. It is also common practice for a clinician to give higher priority to care for the wound than is given to disposal of the needle. In the case of typical needle devices without safety shields, such priority either requires the convenience of an available sharps container within reach or another means for safe disposal, without leaving the patient's side. Thus, the difficulty in providing adequate care while following safety procedures is often compounded by the patient's physical condition and mental state, such as in burn units and psychiatric wards. Under such conditions, proper disposal of a used needle, while caring for a patient, is a technological challenge to the state of the art.

The widespread knowledge and history associated with needle care and disposal problems have resulted in numerous devices for preventing accidental needle sticks. Some devices utilize a separate sheath or cap mounted over the needle after use. These devices, however, require two-handed manipulation from a practitioner.

Other known devices employ sheaths that are spring activated, telescoping, pivoting, etc. These devices, however, may disadvantageously misfire, be inadvertently activated or cumbersome to activate. Further drawbacks of current devices include high manufacturing cost due to complexity and the number of parts. Thus, these type prior art devices may not adequately and reliably shield needle infusion and/or fluid collection apparatus to prevent hazardous exposure.

Consequently, there remains a need to provide a more satisfactory solution for needle safety devices by overcoming the disadvantages and drawbacks of the prior art. Therefore, it would be desirable to provide a more adequate and reliable medical needle shield apparatus which employs an extensible safety shield to prevent hazardous exposure to a needle. Such a needle shield apparatus should be easily and reliably extendable to shield a needle tip of a needle cannula. It would be desirable if the needle shield apparatus was actuated via one handed operation. It would be highly desirable if the medical needle shield apparatus facilitates efficient assembly and manufacture thereof.

SUMMARY

Accordingly, the present disclosure addresses a need for a medical needle shield apparatus which effectively and inexpensively protects a tip of a medical needle after use. The present disclosure resolves related disadvantages and drawbacks experienced in the art. More specifically, the apparatus and method of this invention constitute an important advance in the art of safety needle devices.

In one particular embodiment, a medical needle shield apparatus is provided in accordance with the principles of the present disclosure. The medical needle shield apparatus includes a first cylinder, such as, for example, a shield that is extensible from a retracted position to an extended position for enclosing a distal end of a needle of a medical needle device. The shield includes a collar that is mounted to the medical needle device. The shield further includes a proximal portion extending from the collar and a distal portion extending from the proximal portion. The distal portion is configured to enclose the distal end of the needle in the extended position. The proximal portion includes an engagement surface that is engageable to urge the shield from the retracted position to the extended position. The collar includes a guard extending therefrom and is disposed adjacent to the distal portion of the shield in the retracted position such that inadvertent extension of the shield, via engagement of the distal portion, is prevented.

The collar may include a guard support extending therefrom and supportingly associated with the guard. The distal portion may include a planar portion disposed on the proximal side of the distal portion and protectedly adjacent the guard. The guard prevents the planar portion from being used to extend the shield into the extended position. The guard can be disposed protectedly adjacent the distal portion so as to prevent axial and perpendicular movement of the shield via the distal portion. The guard can be sized and shaped relative to the distal portion to prevent engagement with the distal portion.

Alternatively, the engagement surface includes a manual actuator for manipulating the shield to the extended position. The collar may include a latch that engages a catch on the distal portion to releasably lock the shield in the retracted position. The distal portion may include a fulcrum configured to engage the needle to facilitate the extension of the shield from the retracted position to the extended position. The distal portion may include a planar surface and a nose portion. The nose portion includes at least a portion of the planar surface. The nose portion defines a cavity for disposal of the needle therein. The cavity is defined by side walls and the planar surface. The distal portion can include a lock that engages the needle to fix the shield in the extended position. The proximal portion may include a lock and the distal portion may include a lock which cooperate to fix the shield in the extended position.

In an alternate embodiment, the medical needle shield apparatus includes a first cylinder including a collar. The collar has an inner surface that defines a cavity. The inner surface includes at least one radially inward projecting collar stop. A second cylinder is configured for mounting with a medical needle device. The second cylinder has an outer surface that includes at least one radially outward projecting proximal stop and at least one radially projecting distal stop. The collar is mounted for relative rotational movement with the second cylinder such that the outer surface of the second cylinder is disposed within the cavity of the collar. The at least one collar stop is disposed adjacent the outer surface of the second cylinder such that the at least one proximal stop prevents distal axial movement, relative to a longitudinal axis of the medical needle device, of the collar and the at least one distal stop prevents proximal axial movement of the collar.

The first cylinder may include a shield that is extensible from a retracted position to an extended position for enclosing a distal end of a needle of the medical needle device. The shield may further include a proximal portion extending from the collar and a distal portion extending from the proximal portion. The distal portion is configured to enclose the distal end of the needle.

The collar may include a plurality of collar stops and the second cylinder may include a plurality of proximal stops and a plurality of distal stops. The plurality of collar stops may be equidistantly spaced about the inner surface of the collar and the plurality of proximal stops may be equidistantly spaced about the outer surface of the second cylinder and the plurality of distal stops may be equidistantly spaced about the outer surface of the second cylinder.

Alternatively, the second cylinder may include a press ring that is mounted about the second cylinder in a press fit engagement to fixedly mount the second cylinder with the medical needle device. The second cylinder can be mounted to the medical needle device via an adhesive. Alternatively, the second cylinder includes a cover that has a first cover portion attached to a second cover portion that cooperate to support the medical needle device. The second cylinder further includes a cover base having a grip channel that engages a plunger. The first cover portion can lockingly engage the second cover portion. The grip channel may be disposed adjacent a proximal end of the medical needle device. The first cover portion may be pivotally associated with the second cover portion.

BRIEF DESCRIPTION OF THE DRAWINGS

The foregoing and other features and advantages of the present disclosure will be more fully understood from the following detailed description of the exemplary embodiments, taken in conjunction with the accompanying drawings in which.

DETAILED DESCRIPTION OF THE EXEMPLARY EMBODIMENTS

Figure 1:
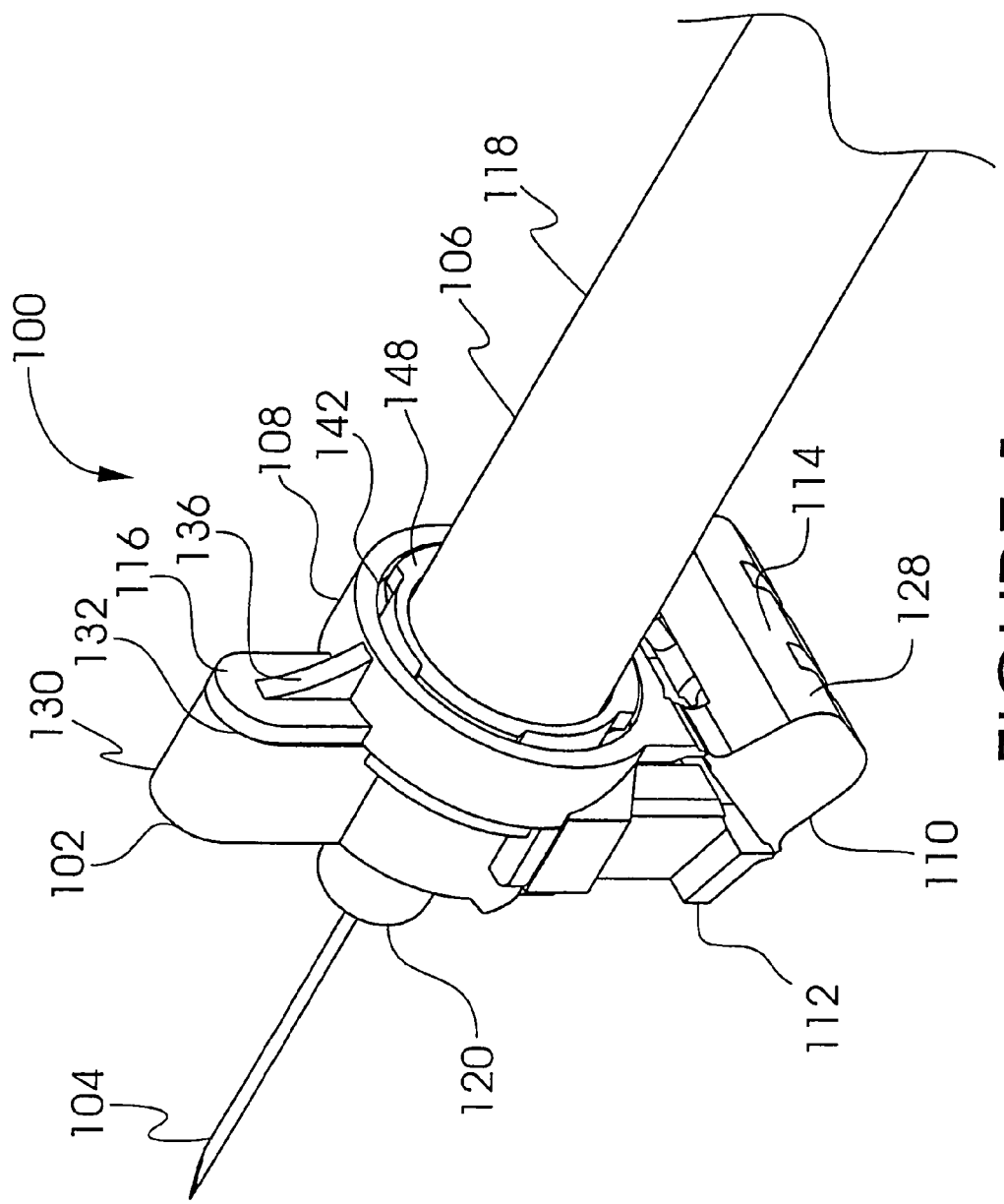
FIG. 1 is a cutaway perspective view of a medical needle shield apparatus in accordance with the principles of the present disclosure.
Figure 2:
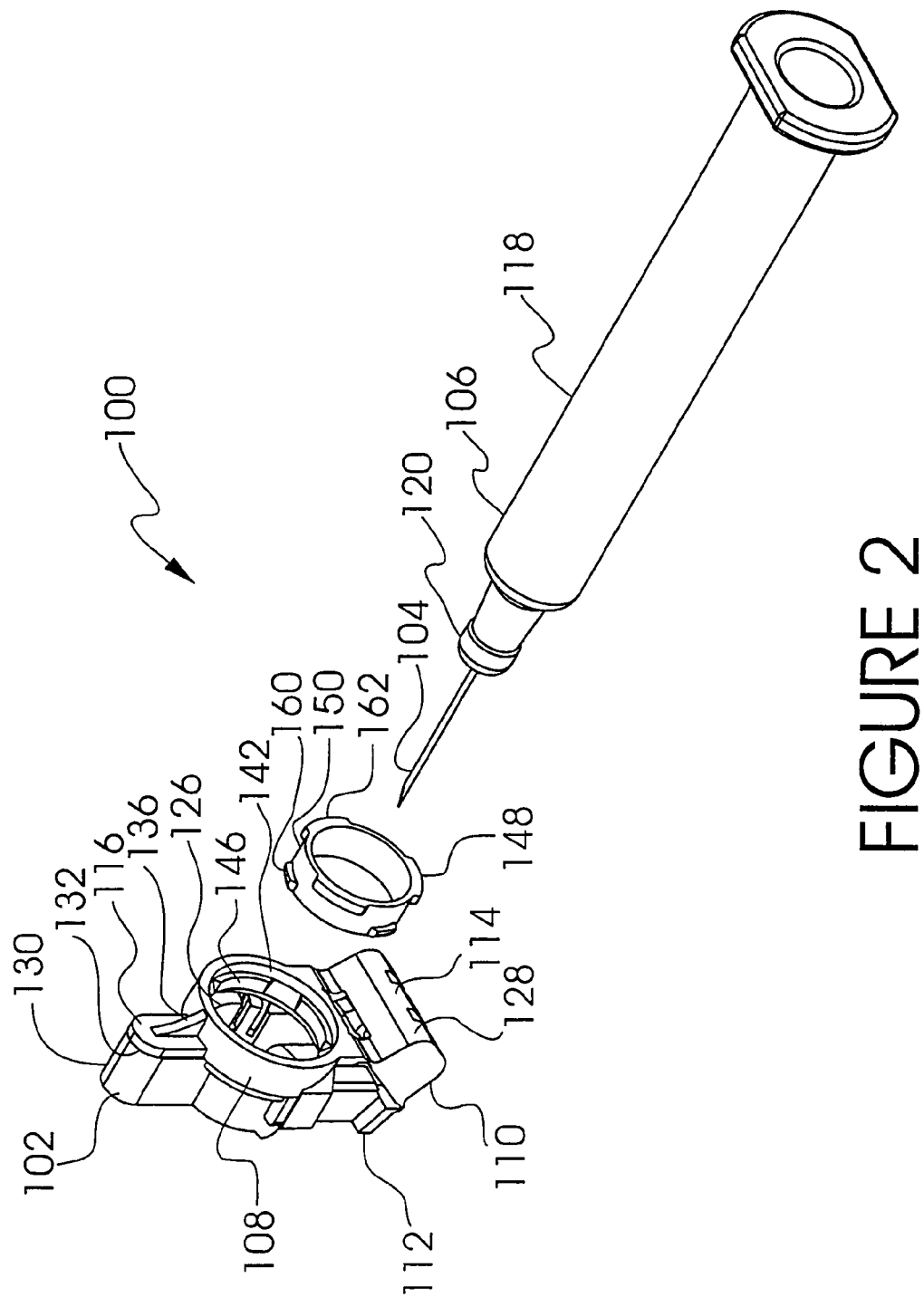
FIG. 2 is an exploded perspective view of the medical needle shield apparatus shown in FIG. 1.
Figure 3:
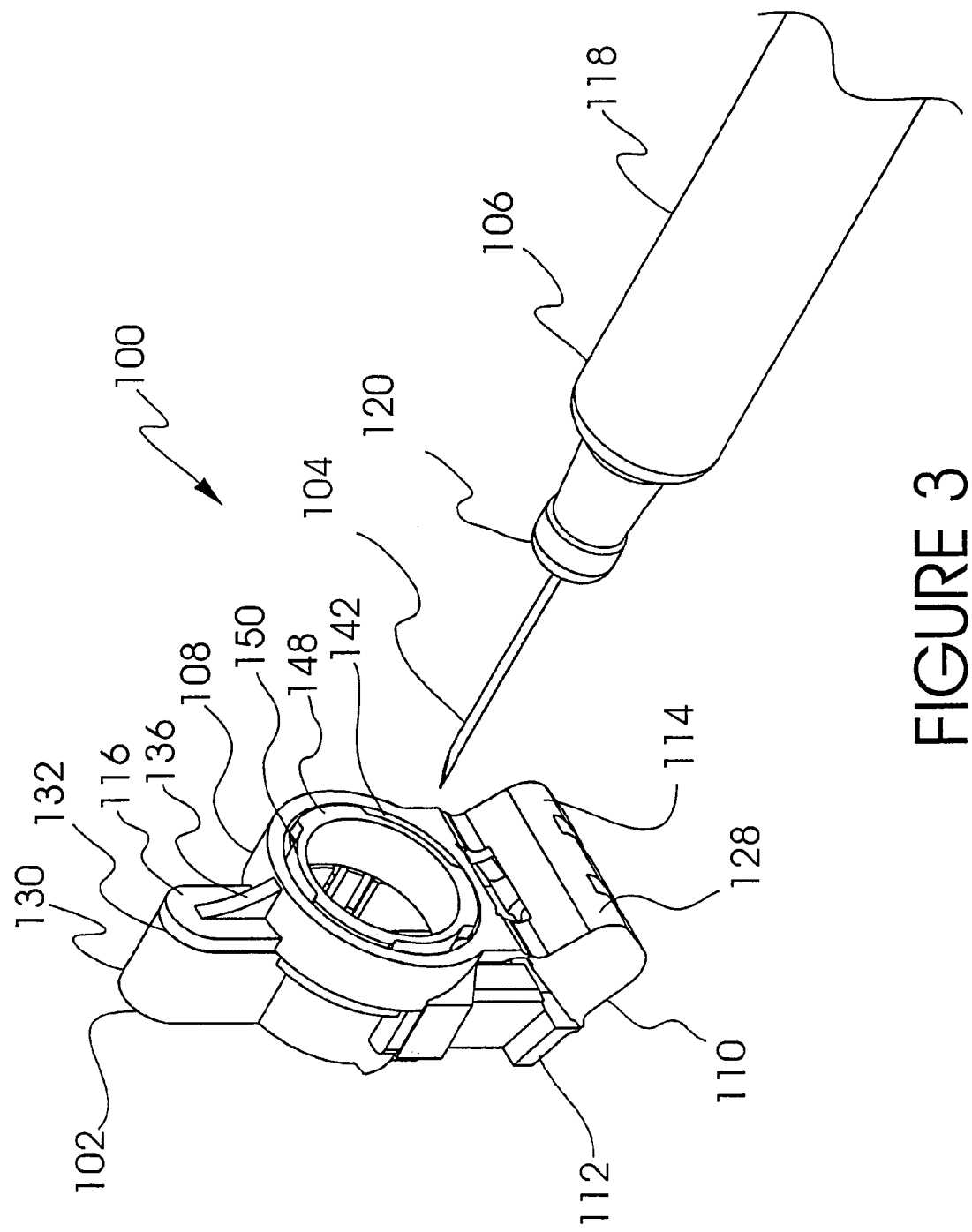
FIG. 3 is a partially exploded perspective view of the medical needle shield apparatus shown in FIG. 1.

The exemplary embodiments of the medical needle shield apparatus and the methods of operation disclosed herein are discussed in terms of medical needles for infusion of intravenous fluids, medication infusion and fluid collection, and more particularly, in terms of a medical needle shield device employed with a needle shield apparatus associated with a needle cannula to prevent damage to the needle and possible hazardous exposure to the needle cannula, for example, through an inadvertent needle stick. It is contemplated that the needle cannula may be shielded during use including storage, transport, fluid infusion and/or collection, subsequent thereto, etc. It is envisioned that the present disclosure, however, finds application to a wide variety of cannula needles and devices for the infusion of preventive medications, medicaments, therapeutics, etc. to a subject. It is also envisioned that the present disclosure may be employed for collection of body fluids including those employed during procedures relating to phlebotomy, digestive, intestinal, urinary, veterinary, etc. It is also contemplated that the medical needle shield device may be utilized with other medical needle applications including feeding devices, phlebotomy devices, catheters, catheter introducers, guide wire introducers, spinal and epidural, biopsy, aphaeresis, dialysis, blood donor, Veress needles, Huber needles, etc.

In the discussion that follows, the term "proximal" refers to a portion of a structure that is closer to a clinician, and the term "distal" refers to a portion that is further from the clinician. As used herein, the term "subject" refers to a patient that receives infusions or has blood and/or fluid collected therefrom using the medical needle shield apparatus. According to the present disclosure, the term "clinician" refers to an individual administering an infusion, performing fluid collection, installing or removing a needle cannula from a medical needle shield apparatus and may include support personnel.

The following discussion includes a description of the medical needle shield apparatus, in accordance with the present disclosure. Reference will now be made in detail to the exemplary embodiments of the disclosure, which are illustrated in the accompanying figures.

Turning now to the figures, wherein like components are designated by like reference numerals throughout the several views. Referring initially to FIGS. 1–4, there is illustrated a medical needle shield apparatus 100 including a first cylinder, such as, for example, a shield 102 extensible from a retracted position to an extended position for enclosing a distal end of a needle 104 of a medical needle device 106. Shield 102 includes a collar 108 mounted to medical needle device 106. A proximal portion, such as, for example, proximal segment 110 extends from collar 108. A distal portion such as, for example, distal segment 112 extends from proximal segment 110. Distal segment 112 is configured to enclose the distal end of needle 104.

It is contemplated that shield 102 may include one or a plurality of segments. Proximal portion 110 includes an engagement surface 114, which is engageable to urge shield 102 from the retracted position to the extended position. Collar 108 includes a guard 116 which extends from collar 108 and is disposed adjacent to distal segment 112, when shield 102 is in the retracted position. This configuration advantageously prevents the inadvertent extension of shield 102 via engagement of distal portion 112.

The components of the medical needle shield apparatus can be fabricated from a material suitable for medical applications, such as, for example, polymerics or metals, such as stainless steel, depending on the particular medical application and/or preference of a clinician. Semi-rigid and rigid polymerics are contemplated for fabrication, as well as resilient materials, such as molded medical grade polypropylene. However, one skilled in the art will realize that other materials and fabrication methods suitable for assembly and manufacture, in accordance with the present disclosure, also would be appropriate.

Collar 108 is circumferentially disposed about medical needle device 106. It is envisioned that collar 108 may have various cross-sectional configurations corresponding to the configuration of medical needle device 106. Guard 116 extends radially outward from collar 108 and has a configuration corresponding to nose portion 130. This adjacent configuration prevents axial engagement with distal segment 112 thereby preventing inadvertent activation of shield 102. It is envisioned that guard 116 may be variously configured and dimensioned to prevent inadvertent activation of shield 102.

Guard 116 may include a guard support 136 that provides increased strength to guard 116 for withstanding inadvertent engagement. Guard support 136 has an angular support configuration and may be variously sized and geometrically configured according to the requirements of a particular needle application. Guard 116 may be monolithically formed with collar 108 or integrally assembled therewith via snap fit, adhesive, etc.

Medical needle device 106 includes, for example, a syringe 118. Syringe 118 has a needle cannula 104 extending therefrom via a needle mount 120.

Distal segment 112 articulates from proximal segment 110 for extension of shield 102 to the extended position. Engagement surface 114 of proximal segment 110 may include a manual actuator 128. Manual actuator 128 is engageable by a clinician for urging shield 102 to the extended position from the retracted position. Manual actuator 128 is articulated from collar 108. As manual actuator 128 is engaged, proximal segment 110 forces distal segment 112 to move distally in a generally axial direction such that distal segment 112 engages needle cannula 104 to facilitate extension of shield 102. Distal segment 112 includes a nose portion 130 having a planar surface 132. In the extended position of shield 102, nose portion 130 substantially encloses the distal end of needle 104 in cooperation with planar surface 132.

Collar 108 has an inner surface 142 that defines a collar cavity 126. Inner surface 142 includes at least one first interlock, such as collar stops 146 that project radially inward. Collar stops 146 are uniformly raised within collar cavity 126 for engagement with a second cylinder, such as, for example, a mounting ring 148. This configuration facilitates mounting of shield 102 with syringe 118. It is envisioned that one or a plurality of collar stops 146 may be used. It is further envisioned that collar stops 146 may be raised or project in a non-uniform manner, such as, for example, staggered, offset, undulating, etc., to include an annular ring.

Mounting ring 148 is configured for mounting with syringe 118. This configuration advantageously facilitates mounting shield 102 with syringe 118. Mounting ring 148 has an outer surface 150 that includes at least one second interlock, such as a plurality of radially outward projecting proximal stops 162 and a plurality of radially outward projecting distal stops 160. Proximal stops 162 and distal stops 160 are equidistantly disposed, circumferentially, about outer surface 150. Proximal stops 162 and distal stops 160 are uniformly raised from outer surface 150 for disposal within collar cavity 126. It is contemplated that one or a plurality of stops 162, 160 may be employed. It is further contemplated that stops 162, 160 may be raised or project in a non-uniform manner, such as, for example, staggered offset, undulating, etc., to include an annular ring. The first and second interlocks prevent movement in both proximal and axial directions. A third interlock may be added to prevent rotational movement.

Mounting ring 148 may be mounted to syringe 118 via an adhesive, such as, for example, pressure-sensitive adhesive, ultraviolet light-activated adhesive, hot-glue adhesive, 1-part and/or 2-part adhesive, rubber cement, "super glue" type adhesives, glue stick type adhesives, air-dry adhesives, press-fit, etc. It is envisioned that no mounting ring may be used. Collar 108 may be similarly mounted to syringe 118.

Collar 108 is mounted for relative rotational movement with mounting ring 148 such that outer surface 150 is disposed within collar cavity 126. Collar stops 146 are disposed adjacent to outer surface 150. Collar 108 is rotated relative to mounting ring 148 such that collar stops 146 are oriented in an interlocking arrangement with proximal stops 162 and distal stops 160. Thus, proximal stops 162 are aligned with collar stops 146 to prevent distal axial movement, relative to a longitudinal axis of syringe 118, of collar 108. Distal stops 160 are aligned with collar stops 146 to prevent proximal axial movement of collar 108.

This configuration advantageously prevents removal of shield 102 from syringe 118. Further, this configuration avoids impedance of administration of fluids via medical needle device 106, during, for example, low-angle subcutaneous injections, etc. Thus, collar 108 is rotatable relative to mounting ring 148, which is mounted to syringe 118, facilitating orientation of the needle bevel of needle cannula 104. This allows selective orientation of the needle bevel relative to shield 102 such that shield 102 does not interfere with positioning during an administration procedure employing syringe 118. It is contemplated that the first cylinder may include shield 102 or mounting ring 148, and that the second cylinder may include shield 102 or mounting ring 148.

Figure 4:
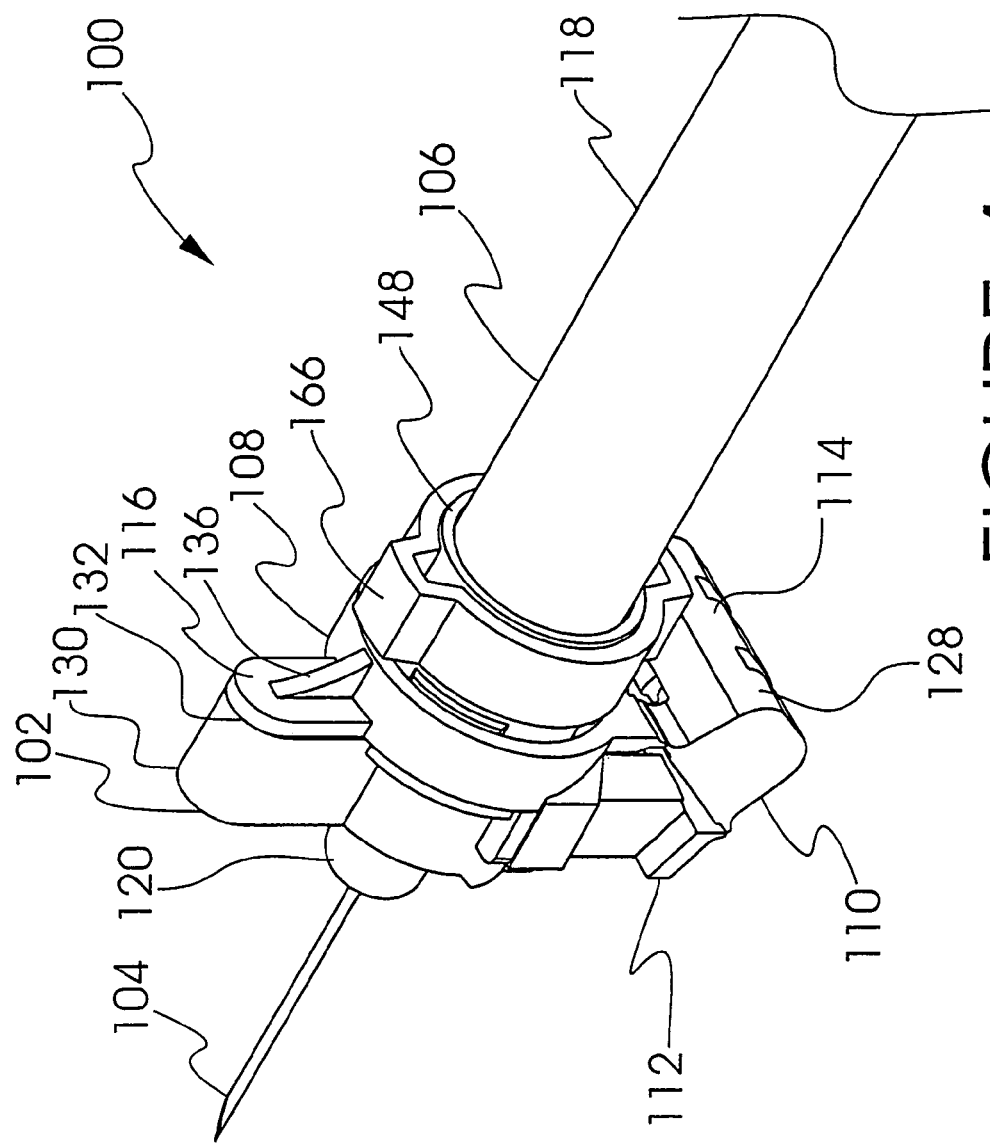
FIG. 4 is a cutaway perspective view of an alternate embodiment of the medical needle shield apparatus shown in FIG. 1.
Figure 5:
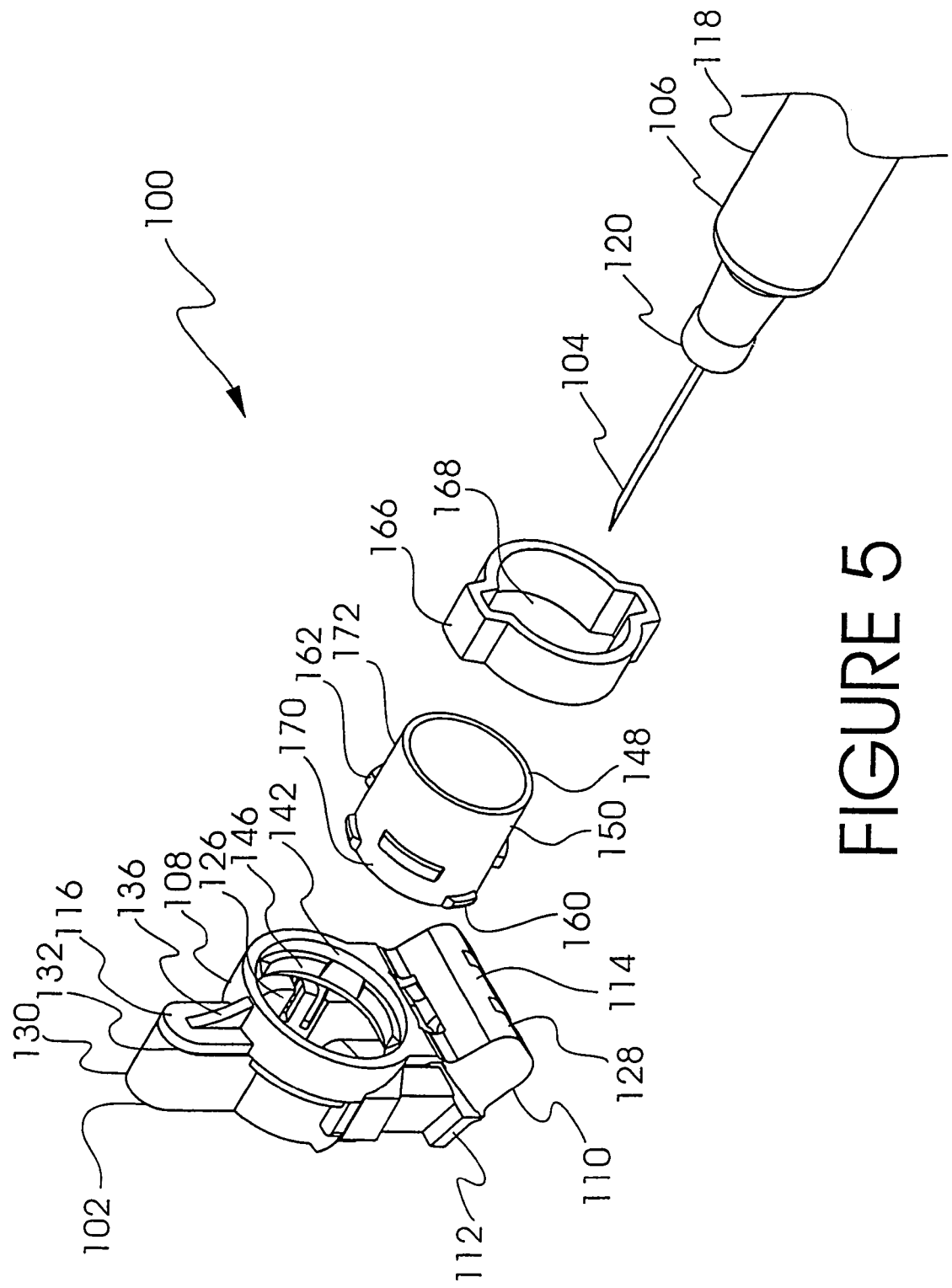
FIG. 5 is an exploded perspective view of the medical needle shield apparatus shown in FIG. 4.

Referring to FIGS. 4 and 5, an alternate embodiment of mounting ring 148 is shown, similar to that described. Outer surface 150 of mounting ring 148 has a collar portion 170 and a clampable portion 172 extending therefrom. Proximal stops 162 and distal stops 160 are formed with outer surface 150. Clampable portion 172 is configured for receiving engagement with a clamp ring 166. Correspondingly, clamp ring 166 defines a clamp cavity 168 for disposal of clampable portion 172 therein. Mounting ring 148 is disposed within collar cavity 126, similar to that described. Clamp ring 166 is configured as a two ear crimp clamp. It is contemplated that clamp ring 166 may be alternatively configured as a one ear crimp clamp, stepless ear clamp, spring clamp, push retainer, push cap, etc.

Clamp ring 166 is manipulated for orientation with syringe 118. Mounting ring 148 is mounted with syringe 118, similar to that described. Clamp ring 166 is fit over clampable portion 172 of mounting ring 148 such that mounting ring 148 is firmly affixed to syringe 118. It is envisioned that clamp ring 166 may be mounted to an interior surface or to outer surface 150 of mounting ring 148. It is further envisioned that clamp ring 166 may be directly employed with collar 108 of shield 102 and may similarly be mounted to an interior surface or an outer surface of collar 108. Clamp ring 166 and collar 108 may be configured so as to create a press fit in which clamp ring 166 and collar 108 are pressed onto syringe 118 as a unit.

Figure 6:
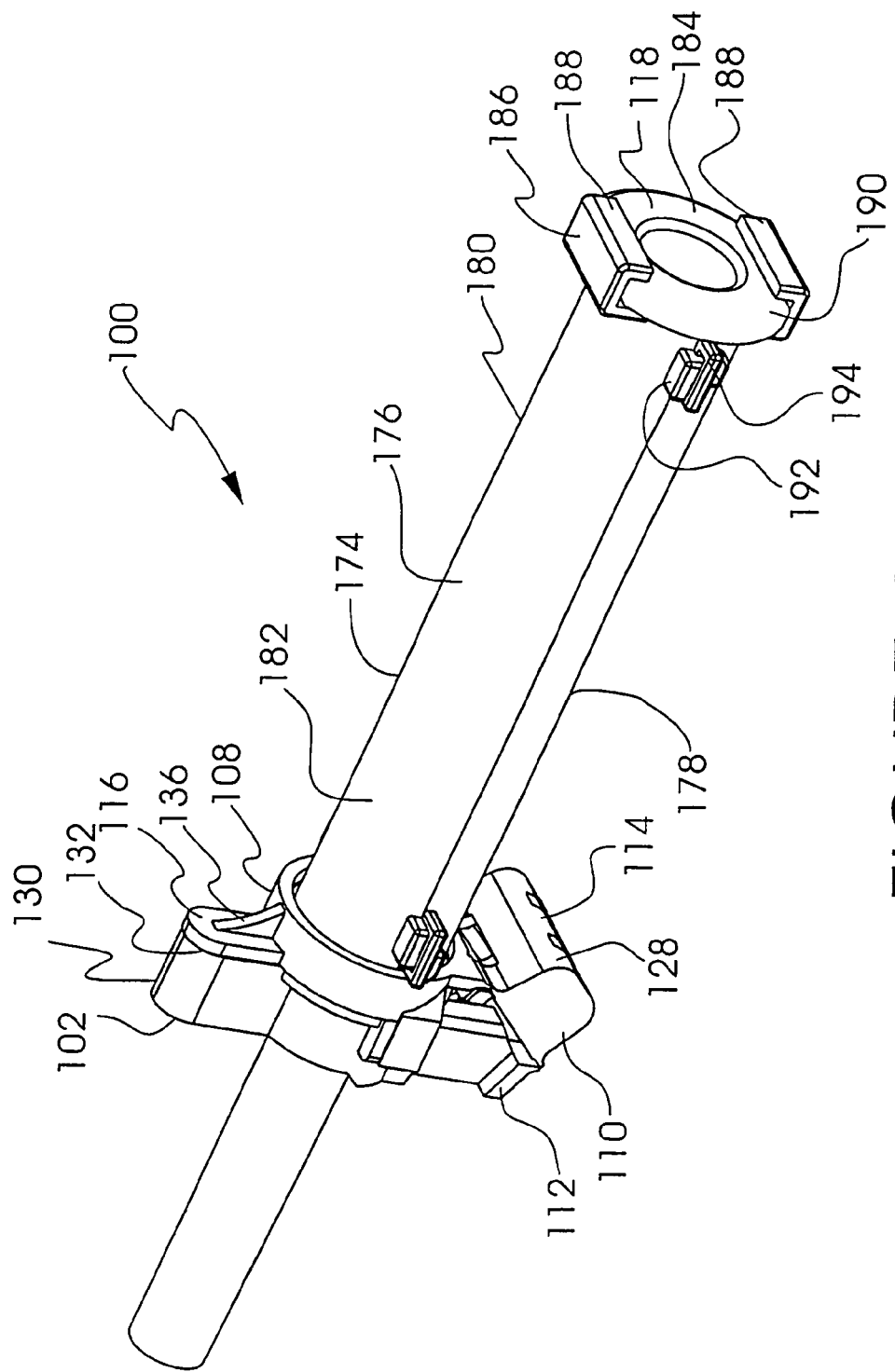
FIG. 6 is a perspective view of another alternate embodiment of the medical needle safety shield apparatus shown in FIG. 1.
Figure 7:
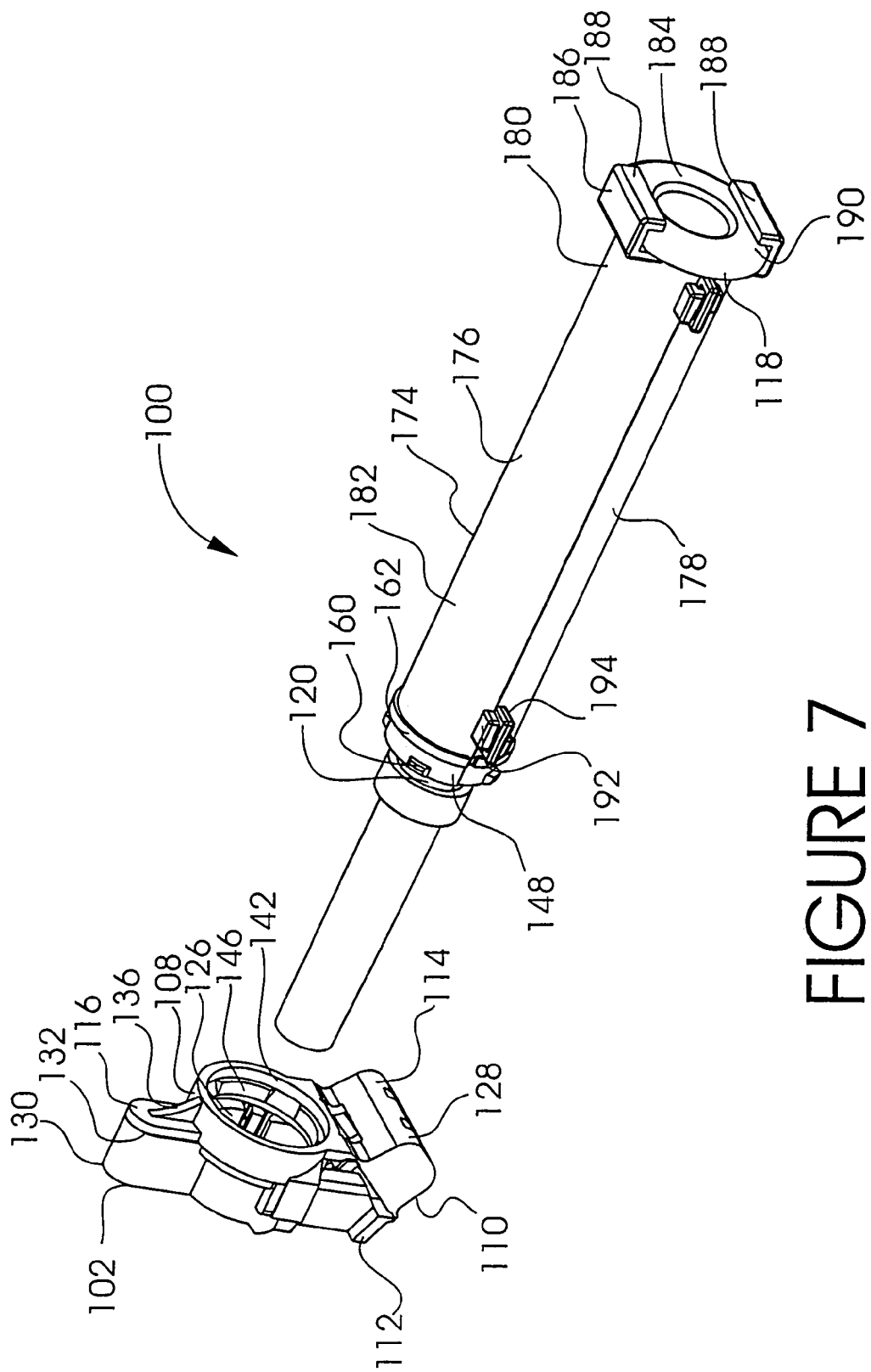
FIG. 7 is a partially exploded perspective view of the medical needle shield apparatus shown in FIG. 6.
Figure 8:
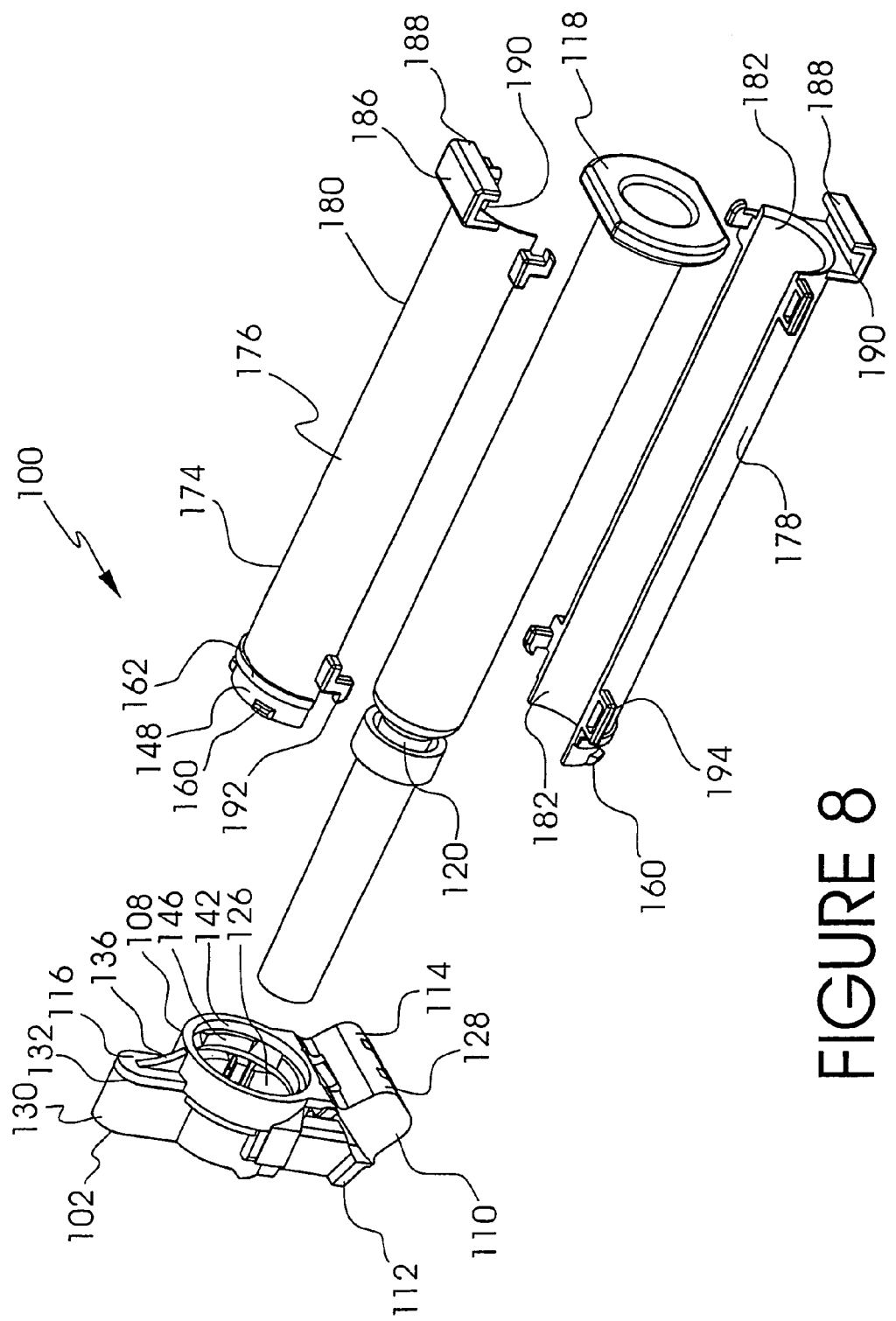
FIG. 8 is an exploded perspective view of the medical needle shield apparatus shown in FIG. 6.

Referring to FIGS. 6–8, another alternate embodiment of mounting ring 148 is shown, similar to those described. Mounting ring 148 includes a cover 174 that has a first cover portion 176 attachable with a second cover portion 178. Cover 174 defines a cover cavity 182 and includes a cover base 180 at a proximal end thereof. Cover 174, and correspondingly cover cavity 182, are configured for attachment to syringe 118. Mounting ring 148 includes proximal stops 162 and distal stops 160, similar to those described, which cooperate with collar 108 to facilitate mounting of shield 102 with syringe 118, as discussed.

Figure 14:
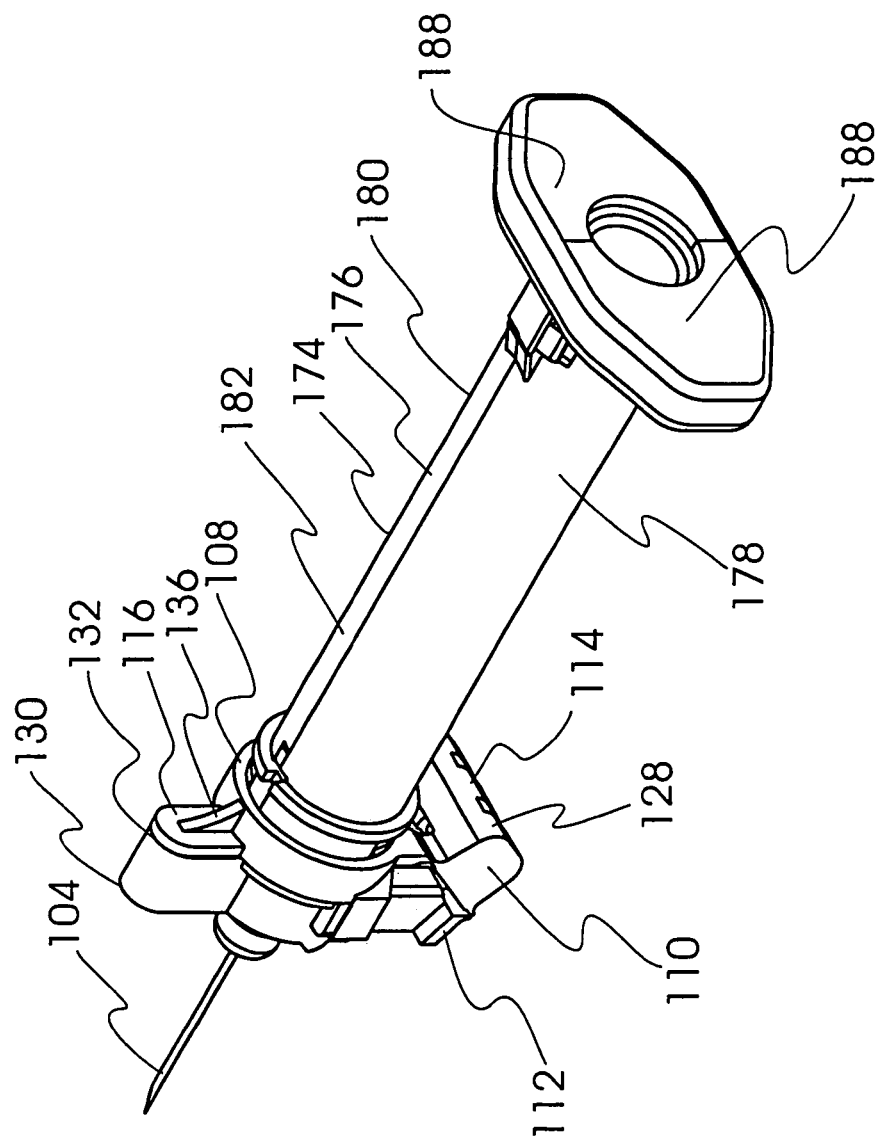
FIG. 14 is a perspective view of another alternate embodiment of the medical needle shield apparatus shown in FIG. 6.

Cover base 180 includes a base opening 184 and a grip channel 186. Grip channel 186 includes grip channel lips 188 that define a grip channel opening 190 configured for receipt of a finger grip of syringe 118. Grip channel lips 188 support the finger grip to facilitate mounting of syringe 118 with mounting ring 148 and prevent rotation of syringe 118 relative to cover 174. It is envisioned that grip channel lips 188 may be configured and dimensioned to support various finger grip configurations, for example, as show FIG. 14. It is also contemplated that the finger grip configurations may be configured to retain a plunger within the syringe barrel as shown in FIG. 14. It is further envisioned that grip channel 186 may include clips, clamps, etc. to facilitate mounting to syringe 118.

Figure 9:
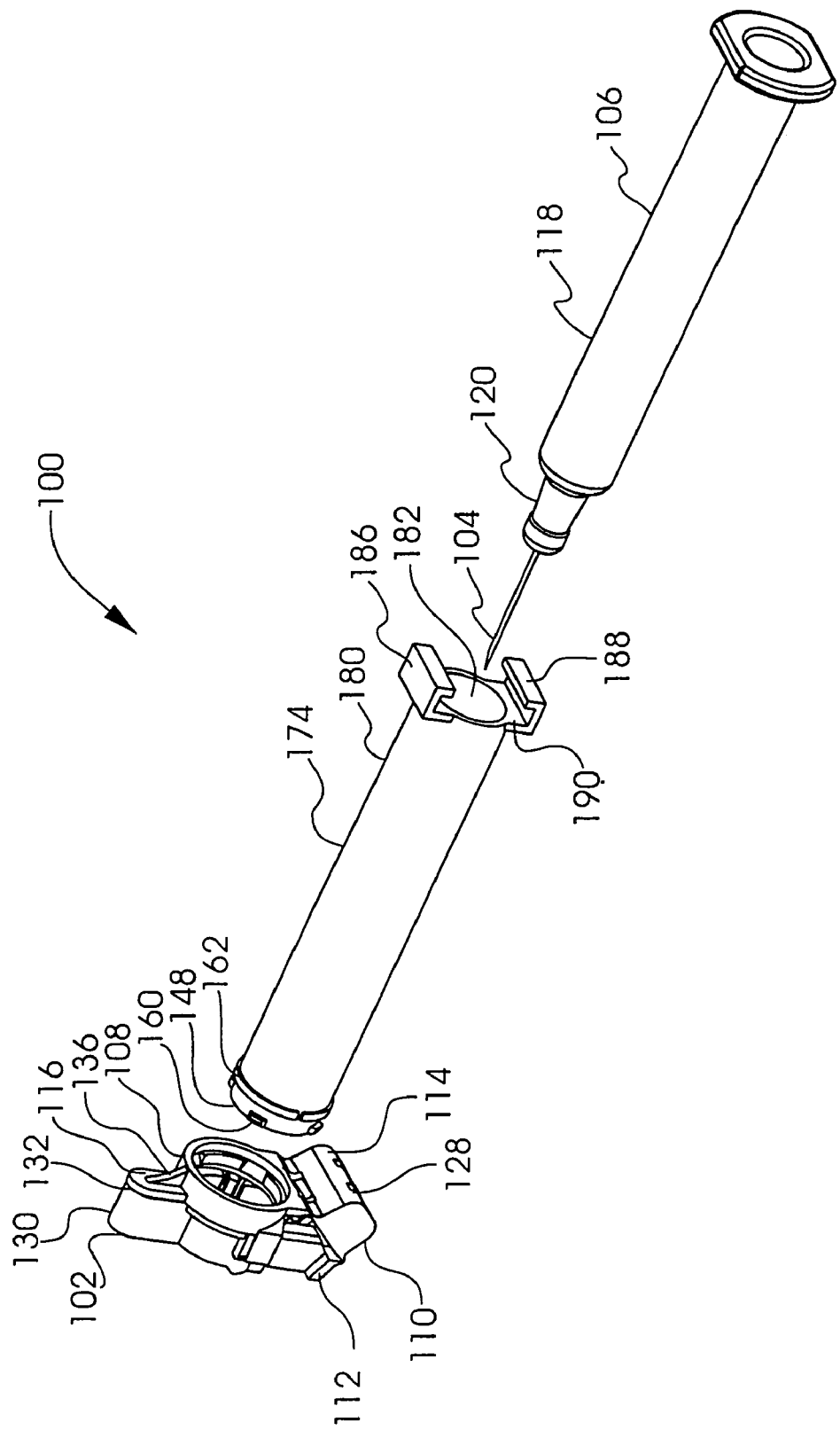
FIG. 9 is an exploded perspective view of alternate embodiment of the medical needle shield apparatus shown in FIG. 6.
Figure 10:
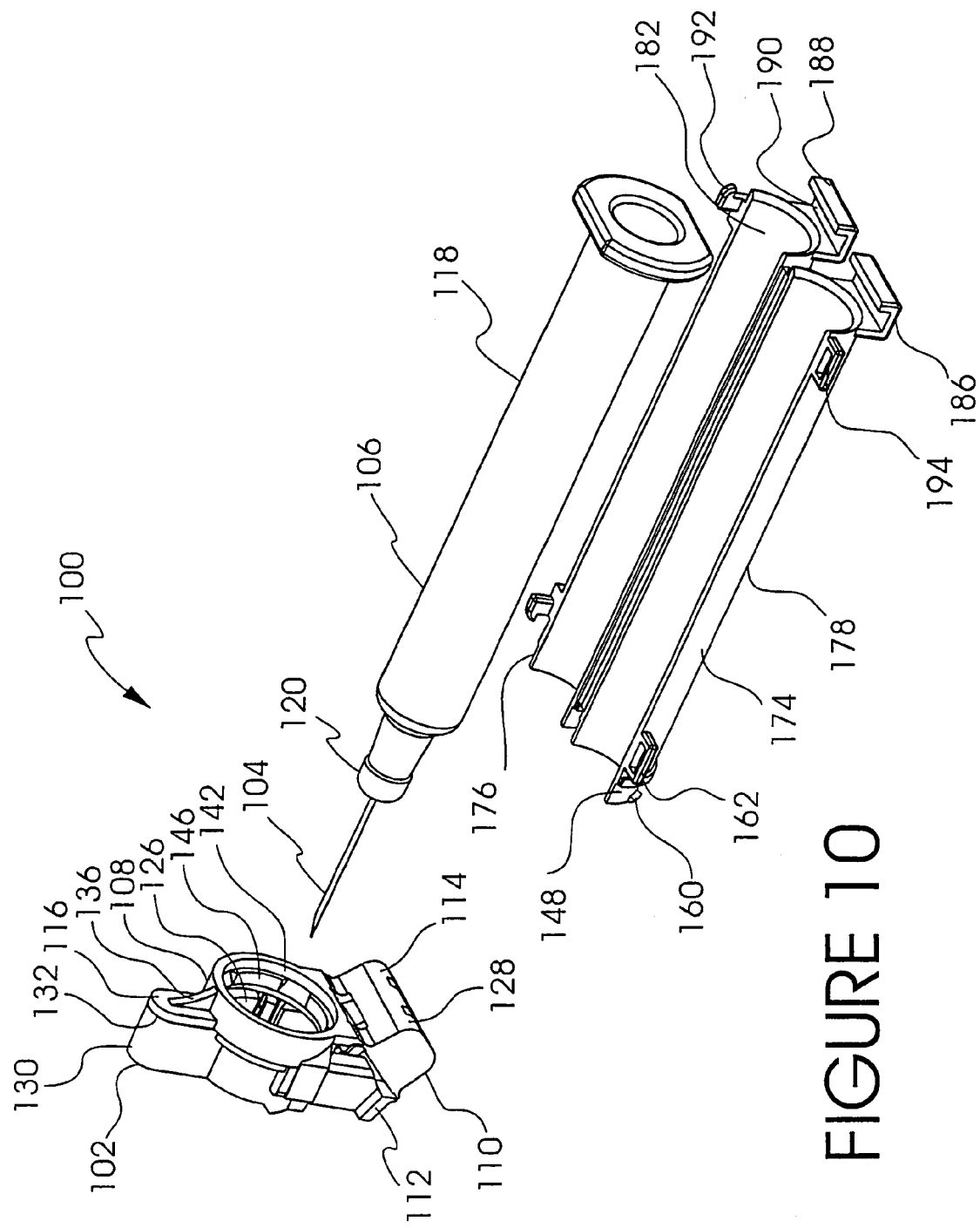
FIG. 10 is an exploded perspective view of another alternate embodiment of the medical needle shield apparatus shown in FIG. 6.

First cover portion 176 and second cover portion 178 are similarly configured and dimensioned for mounting to syringe 118. Portions 176, 178 are elongated half cylinders that extend from a distal end to a proximal end. It is contemplated that cover 174 may have various cross-sectional configurations, such as, for example, polygonal, elliptical, etc. It is further contemplated that first cover portion 176 may be of a dissimilar configuration and dimension than second cover portion 178. A plurality of cover portions may be used or alternatively, each cover portion may be assembled from a plurality of sections. In an alternate embodiment, as shown in FIG. 9, mounting ring 148 includes a cover 174 having a monolithic tube-type sleeve configuration that slides onto syringe 118 for support thereof. In another alternate embodiment, as shown in FIG. 10, mounting ring 148 includes a cover 174 having a first cover portion 176 and a second cover portion 178 that are hingedly connected along its longitudinal length. This one piece clam-shell type configuration is mounted about syringe 118 for support thereof in a locked engagement that employs male tabs 192 and female slots 194.

First cover portion 176 includes a first portion connection device, such as, for example, male tabs 192 and a second portion connection device, such as, for example, female slots 194, which are alternately disposed on either side and at the proximal and distal ends thereof. Second cover portion 178, reciprocal to first cover portion 176, includes male tabs 192 and female slots 194. Tabs 192 and slots 194 of first cover portion 176 are disposed with corresponding slots 194 and tabs 192 of second cover portion 178, respectively, such that first cover portion 176 can be assembled and locked with second cover portion 178. Upon assembly of first cover portion 176 and second cover portion 178, male tabs 192 engage and latch with female slots 194. It is envisioned that one or a plurality of male tab 192/female slot 194 combinations may be employed. It is further envisioned that the male tab 192/female slot 194 combinations may be variously disposed about cover 174. It is contemplated that the cover portions could be joined through adhesive or welding, e.g., sonic, RF, thermal, etc.

Syringe 118 is disposed within cover cavity 182 such that needle cannula 104 protrudes from the distal end of cover 174 and the finger grip of syringe 118 protrudes from the proximal end cover 174. This configuration advantageously allows syringe 118 and syringe cover 174 to rotate relative to collar 108. A rubber sheath is mounted about needle cannula 104 and to needle mount 120 to prevent hazardous exposure to the distal end of needle cannula 104.

Figure 11:
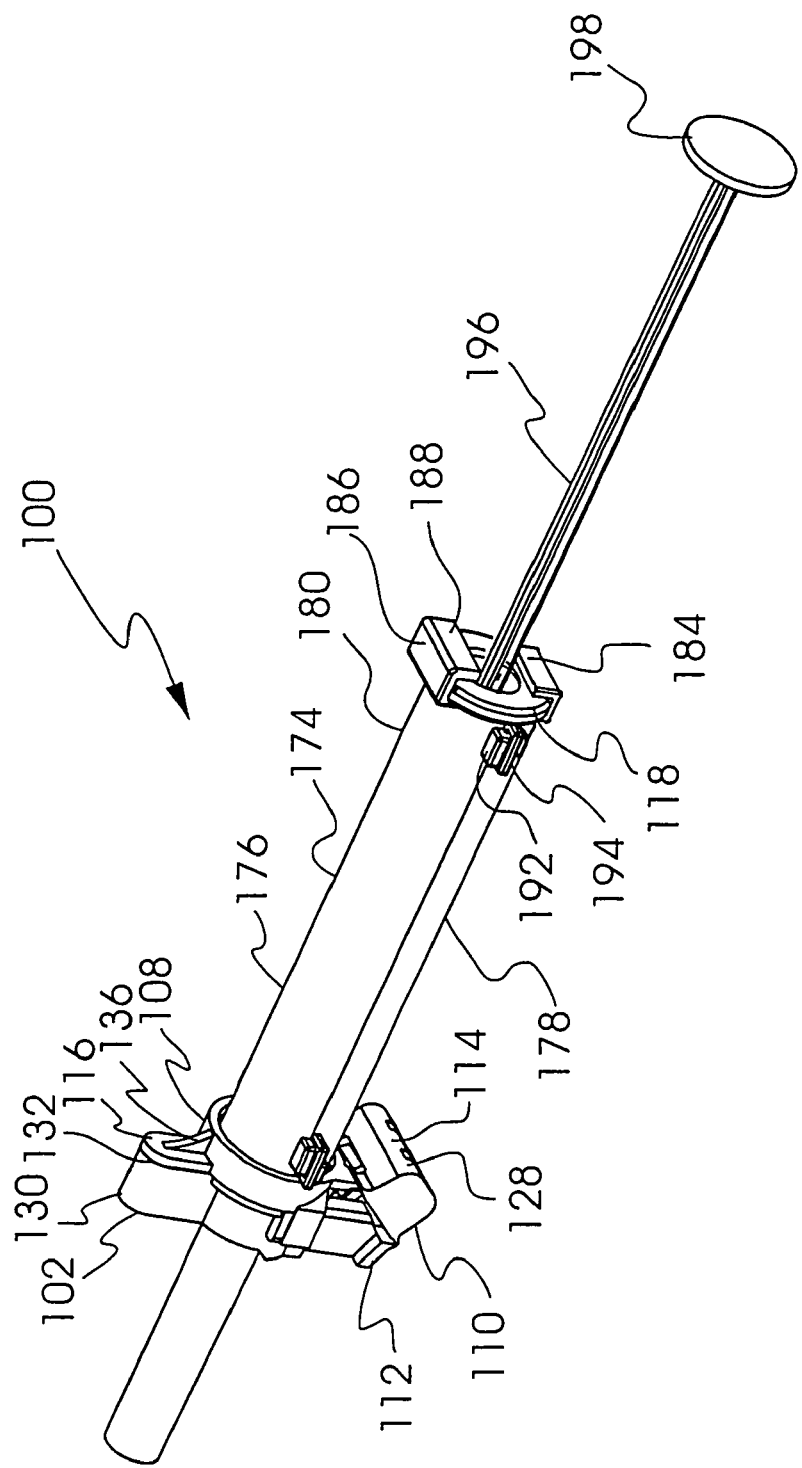
FIG. 11 is a perspective view of another alternate embodiment of the medical needle shield apparatus shown in FIG. 6.
Figure 12:
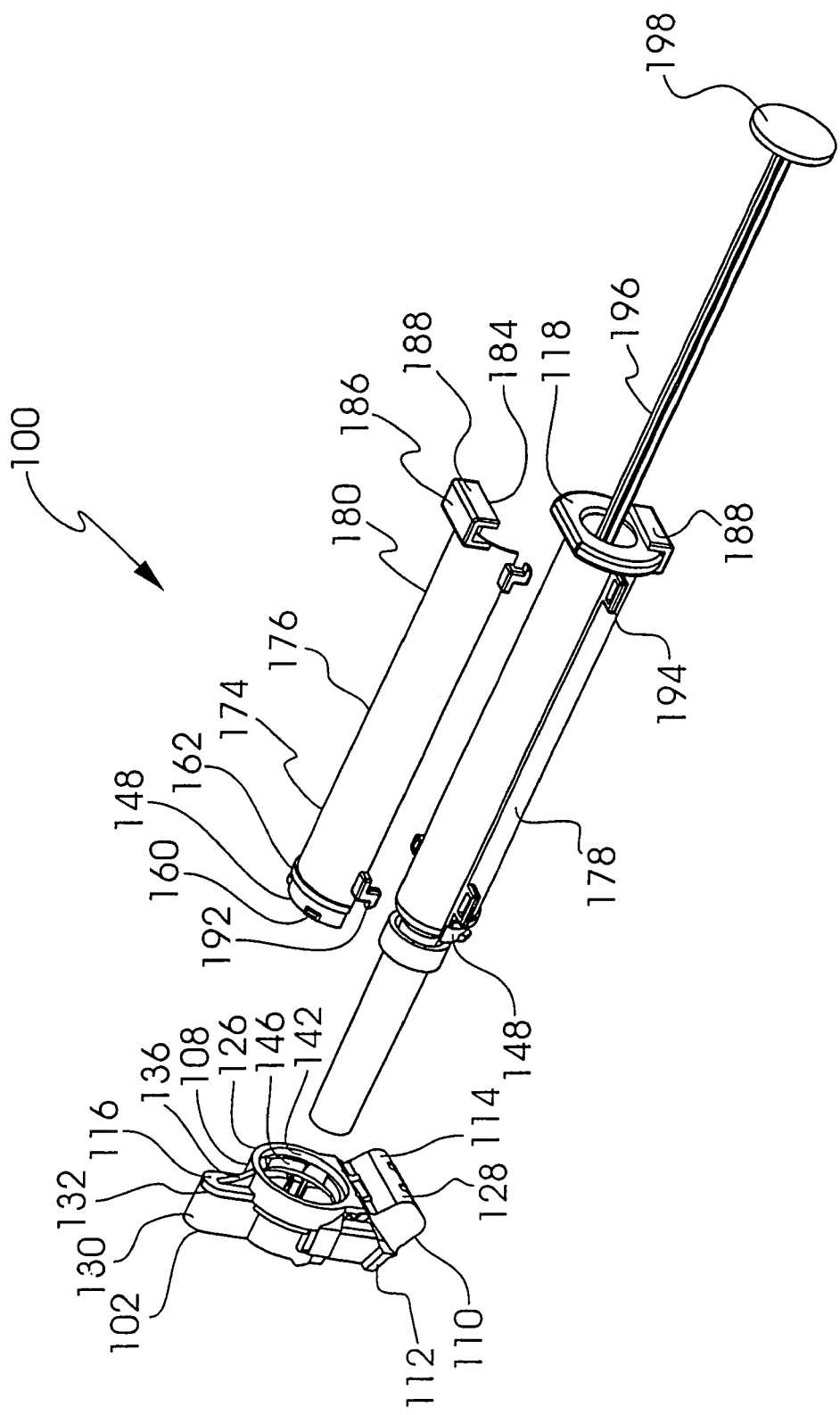
FIG. 12 is a partially exploded perspective view of the medical needle shield apparatus shown in FIG. 11.
Figure 13:
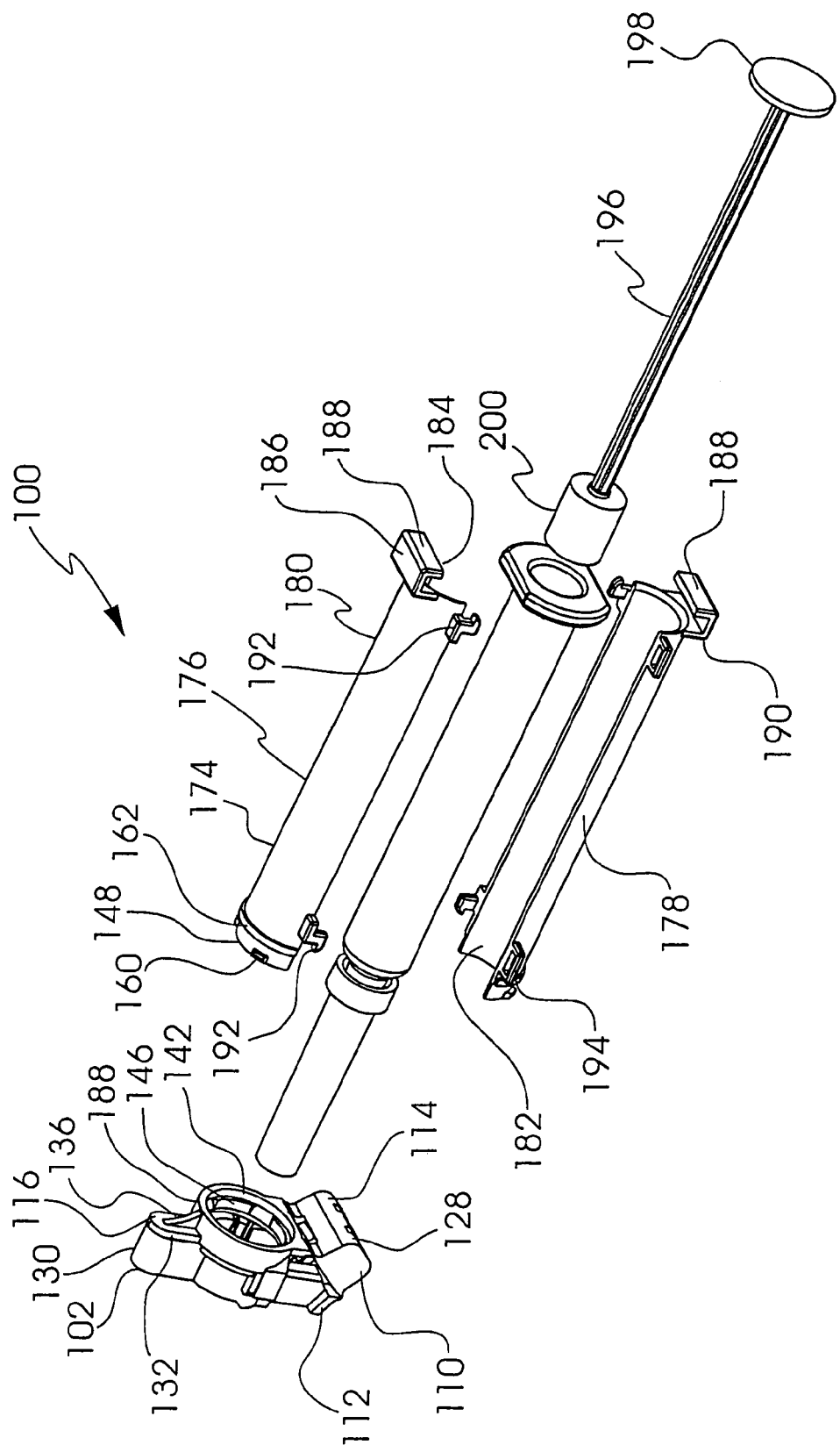
FIG. 13 is an exploded perspective view of the medical needle shield apparatus shown in FIG. 11.

Referring to FIGS. 11–13, in an alternate embodiment, syringe 118 includes a plunger 198 having a plunger rod 196 that extends to a plunger head 200. Plunger 198 is assembled with the barrel of syringe 118 so that upon manipulation of plunger 198, fluids are expelled from syringe 118.

Grip channel lips 188 extend transverse to a longitudinal axis of syringe 118 and radially inward. Grip channel lips 188 converge to define an opening that slidably receives plunger rod 196. The opening, however, is sufficiently dimensioned to prevent proximal movement of plunger head 200 beyond grip channel 186. This configuration advantageously prevents plunger head 200 from being withdrawn from the barrel of syringe 118 and avoids accidental removal of plunger 198 from syringe 118.

The invention of the present disclosure may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A medical needle shield apparatus comprising:
   a shield being extensible from a retracted position to an extended position for enclosing a distal end of a needle of a medical needle device, said shield including a collar that is mounted to said medical needle device, said shield further including a proximal portion extending from said collar and a distal portion extending from the proximal portion, said distal portion being configured to enclose the distal end of said needle in the extended position,
   wherein said proximal portion includes an engagement surface being engageable to urge said shield from said retracted position to said extended position and said collar including a guard extending therefrom and about a distal portion of said medical needle device, said guard being disposed adjacent to said distal portion of said shield in said retracted position such that inadvertent extension of said shield, via engagement of said distal portion, is prevented, wherein said distal portion including a planar surface and a nose portion, said nose portion including at least a portion of said planar surface, wherein said nose portion defines a cavity for disposal of said needle therein, said cavity being defined by side walls and said planar surface.

2. A medical needle shield apparatus as recited in claim 1, said collar further including a guard support extending therefrom and supportively associated with said guard.

3. A medical needle shield apparatus as recited in claim 1, wherein said distal portion includes a planar portion disposed on the proximal side of said distal portion and protectedly adjacent said guard when in the retracted position, whereby the guard prevents said planar portion from being used to extend said shield into said extended position.

4. A medical needle shield apparatus as recited in claim 1, wherein said guard is disposed protectedly adjacent said distal portion so as to prevent axial and perpendicular movement of said shield via said distal portion.

5. A medical needle shield apparatus as recited in claim 1, wherein said guard is sized and shaped relative to said distal portion to prevent engagement with said distal portion.

6. A medical needle shield apparatus as recited in claim 1, wherein said engagement surface includes a manual actuator for manipulating said shield to said extended position.

7. A medical needle shield apparatus comprising:
a shield being extensible from a retracted position to an extended position for enclosing a distal end of a needle of a medical needle device, said shield including a collar that is mounted to said medical needle device, said shield further including a proximal portion extending from said collar and a distal portion extending from the proximal portion, said distal portion being configured to enclose the distal end of said needle in the extended position,
wherein said proximal portion includes an engagement surface being engageable to urge said shield from said retracted position to said extended position and said collar including a guard extending therefrom and about a distal portion of said medical needle device, said guard being disposed adjacent to said distal portion of said shield in said retracted position such that inadvertent extension of said shield, via engagement of said distal portion, is prevented,
wherein said collar includes a latch that engages a catch on said distal portion to releasably lock said shield in said retracted position.

8. A medical needle shield apparatus comprising:
a shield being extensible from a retracted position to an extended position for enclosing a distal end of a needle of a medical needle device, said shield including a collar that is mounted to said medical needle device, said shield further including a proximal portion extending from said collar and a distal portion extending from the proximal portion, said distal portion being configured to enclose the distal end of said needle in the extended position,
wherein said proximal portion includes an engagement surface being engageable to urge said shield from said retracted position to said extended position and said collar including a guard extending therefrom and about a distal portion of said medical needle device, said guard being disposed adjacent to said distal portion of said shield in said retracted position such that inadvertent extension of said shield, via engagement of said distal portion, is prevented,
wherein distal portion includes a fulcrum configured to engage said needle to facilitate the extension of said shield from said retracted position to said extended position.

9. A medical needle shield apparatus as recited in claim 1, wherein said distal portion includes a lock that engages said needle to fix said shield in said extended position.

10. A medical needle shield apparatus comprising: a shield being extensible from a retracted position to an extended position for enclosing a distal end of a needle of a medical needle device, said shield including a collar that is mounted to said medical needle device, said shield further including a proximal portion extending from said collar and a distal portion extending from the proximal portion, said distal portion being configured to enclose the distal end of said needle in the extended position,
wherein said proximal portion includes an engagement surface being engageable to urge said shield from said retracted position to said extended position and said collar including a guard extending therefrom and about a distal portion of said medical needle device, said guard being disposed adjacent to said distal portion of said shield in said retracted position such that inadvertent extension of said shield, via engagement of said distal portion, is prevented,
wherein the proximal portion includes a lock and said distal portion includes a lock which cooperate to fix said shield in said extended position.

11. A medical needle shield apparatus comprising:
an extensible shield assembly having a first cylinder including a collar, said collar having an inner surface that defines a cavity, said inner surface including at least one first interlock; and
a second cylinder configured for mounting with a medical needle device, said second cylinder having an outer surface that includes at least one second interlock, wherein said second cylinder is dimensioned to be rotatably received within said cavity of said collar such that said at least one second interlock is movable into interlocking engagement with said at least one first interlock to axially and rotatably fix the second cylinder in relation to the collar to facilitate selective orientation of the extensible shield assembly relative to the medical needle device.

12. A medical needle shield apparatus as recited in claim 11, wherein said first interlock includes at least one radially inward projecting collar stop.

13. A medical needle shield apparatus as recited in claim 11, wherein said second interlock includes at least one radially outward projecting proximal stop and at least one radially projecting distal stop, such that the at least one proximal stop prevents distal axial movement, relative to a longitudinal axis of the medical needle device, of the collar and the at least one distal stop prevents proximal axial movement of the collar.

14. A medical needle shield apparatus as recited in claim 11, wherein said extensible shield assembly includes a shield that is extensible from a retracted position to an extended position for shielding a distal end of a needle of the medical needle device, said shield further including a proximal portion extending from said collar and a distal portion extending from said proximal portion, said distal portion being configured to shield the distal end of said needle.

15. A medical needle shield apparatus as recited in claim 14, wherein said collar further includes a latch that engages a catch on a distal portion of said shield to releasably lock said shield in a retracted position.

16. A medical needle shield apparatus as recited in claim 11, wherein said at least one first interlock of said collar includes a plurality of collar stops and said at least one second interlock of said second cylinder includes a plurality of proximal stops and a plurality of distal stops.

17. A medical needle shield apparatus as recited in claim 16, wherein said plurality of collar stops are equidistantly spaced about the inner surface of the collar and the plurality of proximal stops are equidistantly spaced about the outer surface of the second cylinder and the plurality of distal stops are equidistantly spaced about the outer surface of the second cylinder.

18. A medical needle shield apparatus as recited in claim 11, further including a clamp ring that is mounted about the second cylinder in a press fit engagement to fixedly mount the second cylinder with the medical needle device.

19. A medical needle shield apparatus as recited in claim 11, wherein the second cylinder is mounted to the medical needle device via an adhesive.

20. A medical needle shield apparatus as recited in claim 11, wherein the second cylinder is mounted to the medical needle device via press-fit.

21. A medical needle shield apparatus as recited in claim 11, wherein the second cylinder includes a cover that has a first cover portion attached to a second cover portion that cooperate to support the medical needle device, the second cylinder further including a cover base having a grip channel.

22. A medical needle shield apparatus as recited in claim 11, wherein the second cylinder includes a cover that has a first cover portion attached to a second cover portion that cooperate to support the medical needle device, the second cylinder further including a cover base having a grip channel that engages a plunger.

23. A medical needle shield apparatus as recited in claim 22, wherein said first cover portion lockingly engages the second cover portion.

24. A medical needle shield apparatus as recited in claim 22, wherein said first cover portion engages the second cover portion via an adhesive.

25. A medical needle shield apparatus as recited in claims 22, wherein said grip channel is disposed adjacent a proximal end of the medical needle device.

26. A medical needle shield apparatus as recited in claim 22, wherein said first cover portion is pivotally associated with said second cover portion.

27. A medical needle shield apparatus as recited in claim 22, wherein said first cover portion and said second cover portion are monolithically formed.

28. A medical needle shield apparatus comprising:

a shield being extensible from a retracted position to an extended position for enclosing a distal end of a needle of a medical needle device, said shield including a collar that is mounted to said medical needle device, said shield further including a proximal portion extending from said collar and a distal portion extending from the proximal portion, said distal portion being configured to enclose the distal end of said needle, wherein said proximal portion includes an engagement surface being engageable to urge said shield from said retracted position to said extended position and said collar including a guard extending therefrom and being disposed adjacent to said distal portion of said shield in said retracted position such that inadvertent extension of said shield via engagement of said distal portion is prevented, the shield further including a collar, said collar having an inner surface that defines a cavity, said inner surface including at least one first interlock; and a mounting ring configured for mounting with a medical needle device, said mounting ring having an outer surface that includes at least one second interlock, said collar being mounted for relative rotational movement with said mounting ring such that the outer surface of said mounting ring is disposed within said cavity of said collar, said at least one first interlock being disposed adjacent the outer surface of the mounting ring such that the at least one second interlock prevents movement in the proximal and axial direction relative to a longitudinal axis of the medical needle device.

29. A medical needle shield apparatus is recited in claim 28, wherein said first interlock includes at least one radially inward projecting collar stop.

30. A medical needle shield apparatus as recited in claim 28, wherein said second interlock includes at least one radially outward projecting proximal stop and at least one radially projecting distal stop, such that the at least one proximal stop prevents distal axial movement, relative to a longitudinal axis of the medical needle device, of the collar and the at least one distal stop prevents proximal axial movement of the collar.

* * * * *